(12) United States Patent
Bennett et al.

(10) Patent No.: US 12,734,358 B2
(45) Date of Patent: Sep. 15, 2026

(54) ANATOMICAL/PHYSIOLOGICAL EVENT APPARATUS AND METHOD OF TREATING AN APPROACHING

(71) Applicants: Jeffrey Bennett, Maple Grove, MN (US); Michael Hoey, Maple Grove, MN (US); Shawn McCutcheon, White Bear Lake, MN (US)

(72) Inventors: Jeffrey Bennett, Maple Grove, MN (US); Michael Hoey, Maple Grove, MN (US); Shawn McCutcheon, White Bear Lake, MN (US)

( * ) Notice: Subject to any disclaimer, the term of this patent is extended or adjusted under 35 U.S.C. 154(b) by 1177 days.

(21) Appl. No.: 17/421,864

(22) PCT Filed: Jan. 10, 2020

(86) PCT No.: PCT/US2020/013193
§ 371 (c)(1),
(2) Date: Jul. 9, 2021

(87) PCT Pub. No.: WO2020/146802
PCT Pub. Date: Jul. 16, 2020

(65) Prior Publication Data

US 2022/0105342 A1 Apr. 7, 2022

Related U.S. Application Data

(60) Provisional application No. 62/954,434, filed on Dec. 28, 2019, provisional application No. 62/841,996, filed on May 2, 2019, provisional application No. 62/790,474, filed on Jan. 10, 2019.

(51) Int. Cl.

| | |
|---|---|
| ***A61N 1/36*** | (2006.01) |
| ***A61B 5/388*** | (2021.01) |
| ***A61N 1/04*** | (2006.01) |

(52) U.S. Cl.
CPC .......... *A61N 1/36007* (2013.01); *A61B 5/388* (2021.01); *A61N 1/0456* (2013.01); *A61N 1/36034* (2017.08)

(58) Field of Classification Search
None
See application file for complete search history.

(56) References Cited

U.S. PATENT DOCUMENTS

| | | | |
|---|---|---|---|
| 1,012,294 | A | 12/1911 | Taylor |
| 4,300,575 | A | 11/1981 | Wilson |
| 6,272,385 | B1 | 8/2001 | Bishay |
| 6,714,824 | B1 | 3/2004 | Ohta et al. |

(Continued)

FOREIGN PATENT DOCUMENTS

| | | | |
|---|---|---|---|
| CN | 118340988 | B | 7/2024 |
| EP | 1279413 | A1 | 1/2003 |

(Continued)

OTHER PUBLICATIONS

The International Search Report and Written Opinion rendered by the International Searching Authority for PCT/US2020/013193, dated Mar. 10, 2020, 14 pages.

*Primary Examiner* — Christine H Matthews
(74) *Attorney, Agent, or Firm* — Skaar Ulbrich Macari, P.A.

(57) ABSTRACT

A neuromodulation device and method capable of varying a neuromodulation therapy in order to prevent, delay or control a sexual emission.

20 Claims, 15 Drawing Sheets

(56) References Cited

U.S. PATENT DOCUMENTS 7,527,589 B2 5/2009 Squicciarini
7,865,250 B2 1/2011 Mrva et al.
8,948,876 B2 2/2015 Gozani et al.
9,149,634 B2 10/2015 Lee
9,821,163 B2 11/2017 Araujo et al.
9,878,154 B2 1/2018 Tai
D810,311 S 2/2018 Chen
9,937,343 B2 4/2018 Nathanson et al.
9,956,405 B2 5/2018 Goldwasser
9,974,593 B2 5/2018 Barman
10,016,600 B2 7/2018 Creasey et al.
D857,205 S 8/2019 Lemons et al.
10,493,264 B1 12/2019 Lefkovitz
10,512,770 B2 12/2019 Wingeier et al.
D879,305 S 3/2020 Gu
10,722,705 B2 7/2020 Cheng et al.
10,773,079 B2 9/2020 Keller et al.
10,806,925 B2 10/2020 Matsushita
10,813,829 B2 10/2020 Liyanage et al.
10,814,131 B2 10/2020 Goldwasser et al.
D909,591 S 2/2021 Lai
11,185,709 B2 11/2021 Kumar et al.
D950,738 S 5/2022 Al-Ali et al.
11,389,369 B2 7/2022 Bennett et al.
11,890,249 B2 2/2024 Jafri
12,161,599 B1 12/2024 Parker
2002/0055702 A1 5/2002 Atala et al.
2002/0082672 A1 6/2002 Janae
2005/0283044 A1 12/2005 Chang
2009/0182396 A1 7/2009 Aller
2010/0298916 A1 11/2010 Rabischong et al.
2011/0288370 A1 11/2011 Orten et al.
2015/0088112 A1 3/2015 Barman
2015/0141880 A1 5/2015 Ehrenreich
2017/0135895 A1 5/2017 Jafri
2018/0110974 A1 4/2018 Deer
2018/0184939 A1 7/2018 Christiansen et al.
2018/0200514 A1 7/2018 Druke
2018/0345003 A1 12/2018 Gollan
2018/0353372 A1 12/2018 Liyanage
2019/0381310 A1 12/2019 Willand et al.
2020/0054285 A1 2/2020 Lemons
2020/0222707 A1* 7/2020 Kumar .................. G16H 50/20
2021/0361941 A1* 11/2021 Gollan ................ A61N 1/0452
2022/0218979 A1 7/2022 Eisenberg
2022/0331142 A1 10/2022 Paz
2024/0207609 A1 6/2024 Ko et al.

FOREIGN PATENT DOCUMENTS

WO 2010059064 A1 5/2010
WO 2017089887 A2 6/2017
WO 2018020246 A2 2/2018
WO 2018060997 A1 4/2018
WO 2018215879 A1 11/2018

* cited by examiner

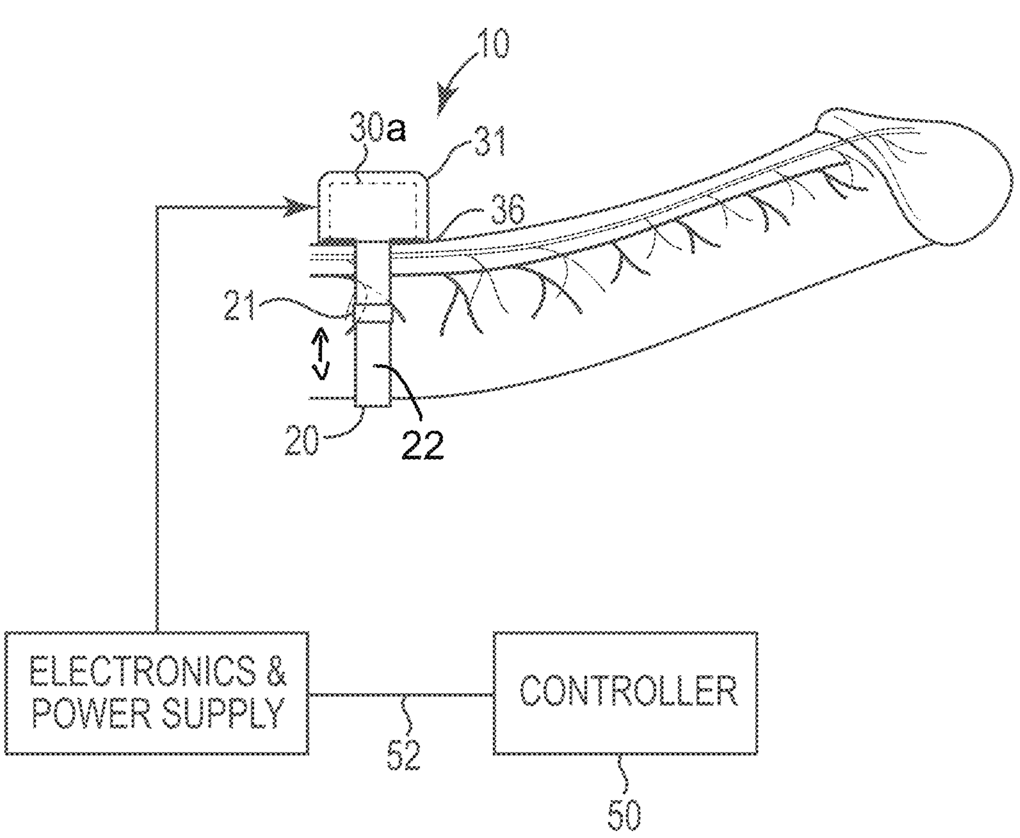
FIG. 1
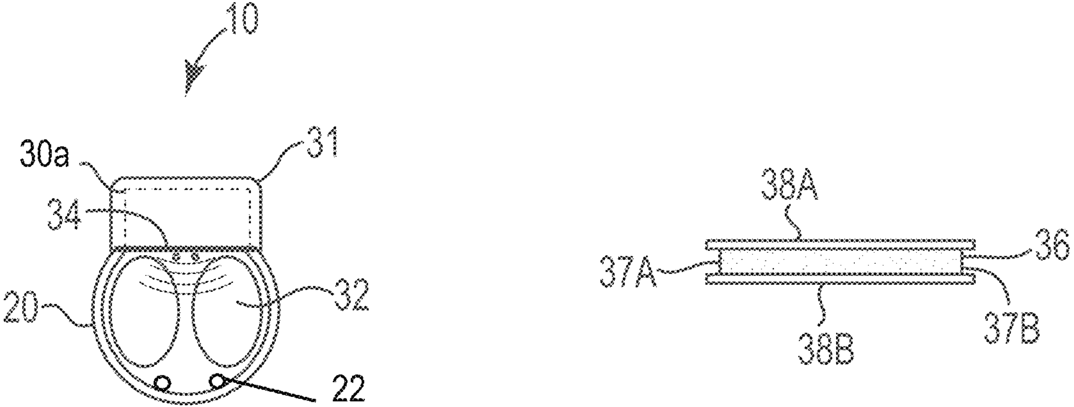
FIG. 2
FIG. 3

ANATOMICAL/PHYSIOLOGICAL EVENT APPARATUS AND METHOD OF TREATING AN APPROACHING

PRIORITY

This Application claims priority to and the benefit of U.S. Provisional Patent Application No. 62/790,474, filed Jan. 10, 2019, U.S. Provisional Patent Application No. 62/841,996, filed May 2, 2019, and U.S. Provisional Patent Application No. 62/954,434, filed Dec. 28, 2019; each of which is incorporated fully herein by reference.

FIELD

The present invention relates generally to the treatment of pelvic health conditions, including but not limited to a sexual dysfunction, such as premature ejaculation, in a male or lack or non-stopping of an orgasm in a female and, more particularly, to an apparatus and method for delaying, ceasing, or stopping an approaching premature ejaculation or orgasmic event.

BACKGROUND

A number of devices and methods are available for enabling those with a sexual dysfunction, such as premature ejaculation, to delay an ejaculatory event. These devices and methods are generally either applied to the surface of the penis, in the form of a pharmacological cream, or are implanted within or proximate to the penis in order to deliver an electrical pulse to a nerve of the penis.

Generally speaking, the methods that are available, or which have been described, include the use of various constriction devices. These devices, like the one described in U.S. Pat. No. 5,921,914 have been used for centuries and are typically applied around a base of a penis to constrict it. The constriction causes the penis to stay erect and prevents the flow of semen. The problem with these constriction devices is that blood is prevented from flowing out of the penis. This permits a blood pooling effect that can causes the temperature of the penis to drop, thereby causing it to feel cold. This can be unpleasant for the person suffering from premature ejaculation and their sexual partner.

In order to overcome the shortcomings of the constriction devices, various compounds were developed to treat premature ejaculation. These compounds have traditionally taken the form of topical anesthetic compounds. The problem with topical compounds is that they are typically applied shortly before a sexual encounter. The application of the topical compound in proximity to a sexual encounter has often resulted in a transfer of the topical compound to a sexual partner. As a result, the partner of an individual suffering from premature ejaculation can be exposed to the compound, thereby desensitizing their sexual organs and delaying or negatively impacting their sexual experience. As such, topical compounds have failed to provide an effective solution to individuals suffering from premature ejaculation.

In order to counter the problems associated with topical compounds, patients have been prescribed antidepressants as a form of treatment. The use of antidepressants has been widely disclosed, including in U.S. Pat. Nos. 4,507,323, 4,940,731, 5,151,448, and 5,276,042. These drugs have had some success; however, their efficacy tends to decrease over time and they are plagued with serious side effects that can cause patients to stop using the drugs.

When topical compounds and drugs failed to provide an adequate solution, medical device companies developed various electrical stimulation devices that stimulate the nerves of the penis in an attempt to prevent premature ejaculation. For instance, in U.S. Pat. No. 7,328,069 to Gerber, Medtronic developed a device that is implantable into an abdomen of a patient, with leads extending into a patient's pelvic cavity to stimulate the pudendal nerve. The problem with these implantable devices is that they carry the shortcomings of all the complications associated with surgery, including, but not limited to, infection. Others developed electrical stimulation devices that did not have to be implanted, but would instead be placed over the penis. These devices, like the one described in U.S. Pat. No. 9,017,244 to Chiu, use cuffs or condom-shaped devices that deliver electrical stimulation to the penis.

Despite all of the devices available or described, a need remains for an improved device and method for treating sexual dysfunction. A device and method of treating a sexual dysfunction, such as premature ejaculation, is needed that doesn't negatively impact the experience of both the sufferer and partner, and that does not require implantation. Additionally, a device and method of treatment that senses an anatomical approaching ejaculatory event and then applies a therapy to stop the event would also be very desirable.

SUMMARY

The present invention is a treatment for pelvic health dysfunctions or sexual dysfunctions, such as, for example, premature ejaculation, which is a condition impacting up to 30% of men worldwide. Various embodiments are configured to sense anatomical physiological changes, such as an approaching ejaculatory event, and then apply a therapy to transdermally stimulate or confuse nerves (e.g., the pudendal nerve) or muscles to stop, cease, or change an anatomical physiological event, such as an ejaculatory event. For the control of ejaculation, the devices and methods described herein stimulate, and thus inhibit, the nerve pathway between the penis and the brain in order to delay ejaculation until the male or female desires to have an ejaculation occur. The entire neural pathway or a portion thereof may be stimulated or treated to impart the therapy provided herein.

In one example embodiment of the invention, a cuff, ring, patch, clip, or similar type of device is removably secured to a portion of the penis, or to another anatomical location effective to treating a condition such as premature ejaculation. The device may be secured to a portion of the penis or the perineum, or another anatomical location to deliver the treatment or therapy. Various devices can include one or more sensors that are capable of sensing an anatomical event, such as an approaching ejaculatory event or other events, such as a sneeze, that may cause incontinence. The sensors are capable of detecting any type of physiological, chemical, or electrical phenomenon related to the anatomical event. For example, the sensors can be configured to detect an increase or change in the girth of the penis or the state of an electrical potential generated by the penis.

The device is able to utilize the detected physiological, chemical, or electrical phenomenon to control the application of the therapy. In one embodiment of the invention, the therapy may consist of a pulsating constriction cuff that is capable of mechanically stimulating the pudendal nerve to cause "ultra" nerve confusion. The cuff can include inner inflatable members that can be inflated and deflated to compress the penis. The cuff can also include a bimetal inner ring or surface that is able to compress the penis and its nerves upon application of an electric current to the device.

The therapy device may include a cuff that is able to deliver a pharmaceutical compound that is able to desensitize the pudendal nerve or dorsal nerve. The cuff is able to apply the compound to the penis or anatomical location and then act as a barrier to a sexual partner to prevent cross exposure. The cuff may also use any of the described embodiments to apply the compound and then to apply pressure to the penis in order to more effectively transmit the compound through the dermis and to the nerve.

The cuff or a similar support device can also comprise a wave producing mechanism generated by an ultrasound source, such as a crystal, to create waves that interfere with various nerves of the penis, or assist in transmitting the compound through the dermis. The waves are transmitted at a frequency that interferes with the signal pathway, thus delaying an ejaculatory event. In another example embodiment of the invention, the cuff may comprise other elements (e.g., electrical, mechanical, chemical or magnetic) that when activated would also interfere with nerve signals from the penis to delay ejaculation.

The present invention may also include a remote wired or wireless controller that controls the delivery of the treatment. For example, the controller can be activated via a dedicated device or a smartphone, watch, or similar device that someone would wear or hold. Anyone having control of the controller would be able to activate or deactivate the therapy device, such as a cuff, ring, or other support structure. When deactivated, the therapy device would not interfere with nerve signals transmitted between the anatomy and physiological event to be treated. When activated, however, the therapy device would cause ultra nerve confusion and prevent an ejaculatory event. The level of nerve signal confusion may be controlled by the person holding or wearing the controller so that the timing of a desired ejaculation can be controlled by either party.

In other embodiments of the present invention, a foldable or hingeable stimulation device can include a housing, a circuit board element, one or more electrodes or pairs of electrodes, and a power supply (e.g., battery). Further, a touch button or other actuation mechanism can be included. The actuation mechanism can be pressed to turn the device on and off, pressed or tapped to increase or vary stimulation, and the like. This device provides non-uniform and changing effective electrical stimulation timing of pulses with varying effective frequencies to "confuse" nerves and receptors involved in the ejaculatory process. The device is hingeable at living hinge portions such that the device can be selectively manipulated and placed with the electrodes contacting the tissue for stimulation. The device can be placed transperineally, with multiple electrodes crossing the plane of nerves running parallel with the urethra.

The above summary is not intended to limit the scope of the invention, or describe each embodiment, aspect, implementation, feature or advantage of the invention. The detailed technology and preferred embodiments for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

BRIEF DESCRIPTION OF THE DRAWINGS

FIG. 1 is a perspective view of the sexual dysfunction treatment system, according to embodiments of the present invention.

FIG. 2 is an end view of the sexual dysfunction treatment system, according to embodiments of the present invention.

FIG. 3 is a cross-sectional view of a coupling member used with a transducer, according to embodiments of the present invention.

DETAILED DESCRIPTION

Figure 4:
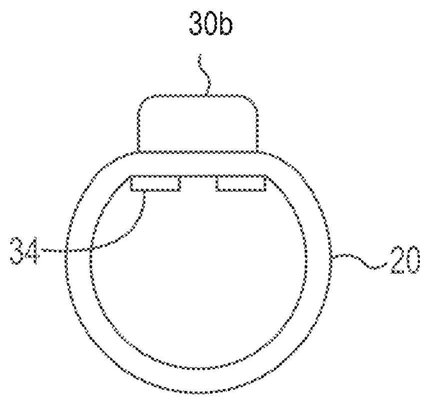
FIG. 4 is an end view of a sexual dysfunction treatment system with an elastic ring or base, according to embodiments of the present invention.

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration rather than to limit the present invention.

Dimensions and relative proportions of components are merely example embodiments and can be varied unless specifically limited in a given claim. Thus, the dimensions can be varied without departing from the scope of the invention.

The present invention illustrates devices, systems, and methods for treating sexual dysfunctions such as premature ejaculation. While the invention is particularly advantageous for patients suffering from a sexual dysfunction such as premature ejaculation, it may also be used by anyone that desires to delay or alter sexual emissions. The present invention may also be used as a means of desensitizing a sexual organ for the purpose of altering sexual activity or emissions. The present invention may have application in humans as well as veterinary applications. Although the present invention is described as being applicable to males, it should be appreciated that the disclosed systems, devices, and methods may also be used to treat a female's pelvic health disorder, including but not limited to, sexual dysfunction and incontinence.

In example embodiments of the invention, as illustrated in FIGS. 1-14, a device, method or physiological event control system 10 is shown for controlling physiological events, such as the premature emission of an ejaculate. In these embodiments, the device 10 includes a ring, base, or cuff 20 or a patch 60 that is removably positionable about a portion of a penis, to a perineum, or another anatomical location of an individual that desires to alter a physiological event such as sexual function—e.g., delaying or altering emissions or climaxes.

The device 10 also includes one or more neuromodulation devices, such as an ultrasound generator 30*a* or an electrical generator 30*b*, attached to or incorporated as part of the cuff 20 or patch 60. The ultrasound generator 30*a* or electrical generator 30*b* generates energy that causes nerve confusion within the pudendal nerve or dorsal nerve of the penis. The nerve confusion causes a change in sexual function (i.e., delay in an ejaculatory event). It should be noted that other neuromodulation devices, such as mechanical stimulation devices, may also be used and should be considered to be within the spirit and scope of the invention.

One of the purposes of the cuff 20 or patch 60 is to position the ultrasound generator 30*a* or electrical generator 30*b* proximate to a portion of a sexual organ, such as a penis or perineum, to be treated. As will be discussed in more detail below, in one embodiment of the present invention, a controller 50 is provided that controls the ultrasound generator 30*a* or electrical generator 30*b* and other features of the present invention.

An important feature of these devices is its ability to sense an approaching ejaculatory event and then to apply a therapy. The therapy device 10 includes one or more sensors 22 that are capable of detecting any type of physiological, chemical, or electrical phenomenon related to the ejaculatory event. For example, the sensors 22 are able to detect an increase or change in the girth of the penis or a state of an electrical potential generated by the penis.

As illustrated in FIG. 1, in a ring or cuff 20 embodiment of the present invention, the ring or cuff 20 may extend about a circumference of a patient's penis. In one of the methods of treating or delaying sexual emissions, the ring or cuff 20 may be positioned generally close to a base of the penis. However, the ring or cuff 20 may be placed at or along any location of the sexual organ that may provide effective therapy. It should be noted that the location of effective therapy may be different for different individuals and treatment applications.

The sensor 22 of the ring or cuff 20 may comprise a band that extends about a circumference of the penis. As an ejaculatory event approaches, the penis generally changes shape or size. A rate of these changes can increase in time as an ejaculatory event grows near. The sensor 22 is able to detect these changes and begin to apply a therapy to cause nerve confusion, and thus delay ejaculation.

The ring or cuff 20 may comprise a generally elastomeric material such that it can be stretched over the sexual organ prior to or during use. The ring or cuff 20 may be manufactured from a durable yet supple material such as silicone. As the device 10 may be worn during intercourse, the ring cuff or 20 should ideally have a profile that is either not noticable by a partner or is enjoyable to the partner. Lastly, the material of the ring or cuff 20 permits it to be easily cleaned after use.

The ring or cuff 20 may also be adjustable to permit it to be adjusted to accommodate users of various sizes. The ring or cuff 20 may be manufactured with various features that permit it to be adjustable. In an example embodiment, the ring or cuff 20 may have a pair of opposed free ends that may be coupled together by a coupler 21. Other adjustable mechanisms are also possible and the embodiments presented herein should not be considered limiting.

As illustrated in FIG. 2, the ring or cuff 20 is used to support the ultrasound generator 30*a* or electrical generator 30*b*, as well as power source. In various examples, the ultrasound generator 30*a* or electrical generator 30*b* is non-implantable and configured to generate an ultrasound output or wave 32, or an electrical current in response to an approaching ejaculatory event.

A driving signal is provided by the controller 50 that is in operative communication with the sensor 22. The controller 50 controls the amount of energy emitted and is also able to control a pattern of energy emitted or applied to the sexual organ or penis. The controller 50 may be in communication with the ultrasound generator 30*a* or electrical generator 30*b* either wirelessly or by a connection 52.

For an ultrasound generator 30*a* or electrical generator 30*b*, ultrasound energy or electrical energy, is applied to the surface of the tissue of the penis by one or more energy emitting surface or probes 34. As illustrated in FIG. 2, energy emitting surface or probes 34 can be in direct physical contact with the tissue of the penis or sexual organ. In other embodiments, the energy emitting surface 34 can be positioned proximate the tissue of the penis or sexual organ. Although depicted near a superior or top surface of a penis, the probes 34 can be placed in any therapeutically effective location on the cuff 20.

The ultrasound generator 30*a* or electrical generator 30*b* is configured to emit energy at frequencies or currents needed to deliver the effective therapy. The controller 50, through the sensors 22, is able to detect if an applied therapy is being effective. For instance, the controller 50 is able to detect if there is a decrease in the physiological, chemical, or electrical potential characteristics of the penis. If no change is detected, the controller 50 may increase the amount of energy being applied to the organ.

As particularly illustrated in FIG. 2, the emitted energy, regardless of type, may be aligned generally normal with the emitting surface of the probes 34. However, in other example embodiments, emitting elements 34 may be generally aligned at varying angles.

The ultrasound generator 30*a* or electrical generator 30*b* may be positioned in a housing 31 made of a durable material such as polyvinyl chloride (PVC), polypropylene (PP), polyethylene (PE), polystyrene (PS) as well as nylon polyethylene terephthalate (PET), polyimide (PA), polycarbonate (PC), acrylonitrile butadiene (ABS), polyetheretherketone (PEEK) and polyurethane (PU), to name a few. The ultrasound generator 30*a* or electrical generator 30*b* and its housing are ideally resistant to fluids and can be easily cleaned. The ring or cuff 30 may also be manufactured from a similar or dissimilar material as the housing 31. The housing 31 permits a user to remove the ultrasound generator 30*a* or electrical generator 30*b* for the purpose of replacement or repair.

When the ultrasound generator 30*a* or electrical generator 30*b* is activated, it emits energy (wave or current) 32 toward a nerve, for example a dorsal nerve or pudendal nerve, that causes it to be stimulated or inhibited. In the present invention, the controller 50 is able to change the intensity and pattern of the energy flowing through the probes 34. The ability to change the intensity and pattern of the energy enables the confusion of the nerves being targeted. The nerve confusion prevents the nerve signal, indicating an approaching ejaculatory event, from traveling to the brain. In one embodiment of the invention, the controller 50 is able to continuously alter the intensity and pattern to adapt in the event the body adapts to the stimulus and begins to send the nerve signal, indicating an ejaculatory event, to the brain.

The ultrasound generator 30*a* generally consists of a generator that responds to a high-frequency alternating current. The high frequency electric current is then converted by the ultrasound generator 30*a* into mechanical (acoustic) vibrations. The ultrasound generator 30*a* consists of a crystal inserted between two electrodes. As an alternating electrical charge is applied to the surfaces of the crystal, the crystal is made to vibrate rapidly, thereby creating sound waves.

In yet another embodiment of the invention, the ultrasound generator 30*a* can generate an energy wave or vibration through a coupling medium. It is known that ultrasound waves are transmitted more effectively through water, oil, or transmission gel, than through air. Consequently, as illustrated in FIG. 3, a coupling member 36 may be used to "couple" the emitting surface 34 of the ultrasound generator 30*a* to the patient's penis in order to ensure that the ultrasound waves are properly transmitted to the desired treatment site. The coupling member 36 may, for example, be in the form of a gel or lotion which is applied to the skin of the patient over the area to be treated. The ultrasound generator 30*a* may then be positioned on the coupling member 36, and the generator is activated. Ultrasound waves 32 produced at the emitting surface 34 are transmitted through the coupling member 36 into the patient to stimulate the dorsal nerve or pudendal nerve.

In another example embodiment of the invention, the coupling member 36 may comprise a sheet, pad, or disk of material that is capable of transferring sound waves into the penis of the patient. The coupling member 36 may have generally opposed planar surfaces 37A, 37B that permit the planar surfaces to be placed against the skin of the patient's penis and the emitting surface 34 of the transducer 30. The planar surfaces 37A, 37B may be covered by a film member 38A, 38B that permit the surfaces of the coupling member 36 to remain free of debris. In embodiments where the coupling member 36 comprises a solid or semi solid material, such as a gel, the films 38A, 38B permit the coupling member 36 to retain its moisture content. These pads or coupling member 36 can be sold together with the transducer or sold separately to permit a user to reuse the system device or system 10.

The properties of the ultrasound generator 30*a* depend upon its diameter and frequency. For example, a small diameter produces a generally small diameter ultrasound beam. In an example embodiment of the invention, ultrasound frequencies of about 400 khz may be used to stimulate the dorsal nerve or pudendal nerve. A range of ultrasound frequency to include 0.5 to 3 MHz may also be used to treat the nerve. A practitioner may use the controller 50 to select a particular frequency depending upon the dimension of the patient.

In an example embodiment of the invention, the other parameters of the device 10 may comprise:

- a pulse width of 1 msec, and a treatable range of 0.01 to 5,000 msec
- a stimulation frequency of 100 Hz
- an ultrasound treatable range of 0.5 to 3 MHz or 0.5 to 5 MHz
- an acoustic power in a treatable range of 400 W/cm$^2$ to 7,500 W/cm$^2$ Other treatable ranges are possible and may be used to treat various conditions. Therefore, the above-cited ranges should not be considered limiting.

Although the device 10 of the present invention includes the controller 50 that is able to automatically control the therapy provided, it can also be at least partially controlled by a user or partner. For instance, the controller 50 can be used to activate the ultrasound generator 30*a* or electrical generator 30*b* or other elements within the ring or cuff 20. The controller 50 can also be used to turn off the ultrasound generator 30*a* or electrical generator 30*b* by the person being treated, or their partner. Turning off the ultrasound generator 30*a* or electrical generator 30*b* ceases the therapy and allows for or permits an ejaculatory event. By providing at least limited control of the controller 50, a user or their partner is able to alter the sexual function, such as delaying ejaculation, until a desired period of time. This control ensures that both parties are able to achieve the sexual satisfaction that they desire.

The system may include a mobile device (e.g., smartphone or other device) in operative communication with the controller 50. However, any other type of control device may be used, including but not limited to wireless smart watches and the like. The device 10 may also use a controller 50 that is dedicated to the ultrasound generator 30*a* or electrical generator 30*b*. This dedicated device may be wired or wireless. Independent of the type of controller 50 utilized, it should have the functionality to control (e.g., turn on and off the ultrasound generator 30*a* or electrical generator 30*b*, receive feedback, monitor data, log data, control or adjust output, etc.) the device or system 10.

Figure 5:
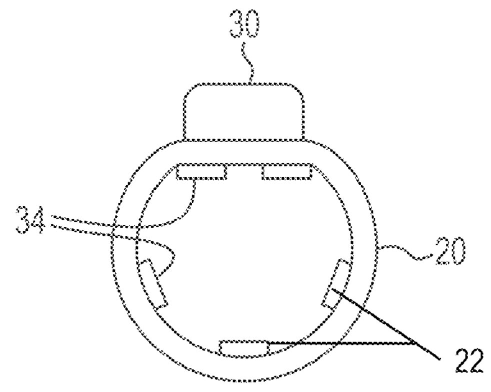
FIG. 5 is an end view of a sexual dysfunction treatment system with an array of transducers, according to embodiments of the present invention.
Figure 6:
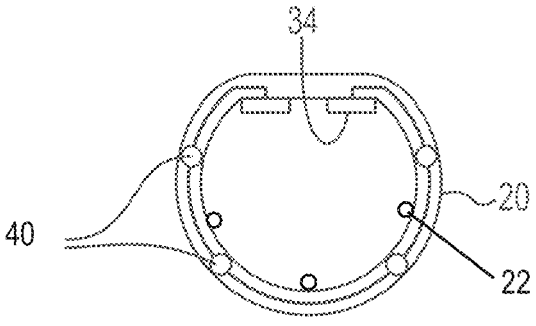
FIG. 6 is a cross-sectional view of a sexual dysfunction treatment system with one or more power supplies embedded within a ring, according to embodiments of the present invention.

As illustrated in FIGS. 4-6, the ring or cuff 20 may incorporate the ultrasound generator 30*a* or electrical generator 30*b*, probes 34, other elements (such as power supplies 40) and sensors 22 into its construction so that its profile is minimized. As particularly illustrated in FIG. 4, the probes 34 are positioned proximate the ultrasound generator 30*a* or electrical generator 30*b*. In this embodiment, a user uses the position of the housing 31, and thus the probes 34, to correctly position the device or system 10 at a particular therapy location.

In another embodiment of the invention, as illustrated in FIG. 5, the ring or cuff 20 may include a plurality of probes 34 and sensors 22 positioned about the cuff 20. The probes 34 are operatively coupled to the ultrasound generator 30*a* or electrical generator 30*b* to emit energy about the circumference of the cuff 20. In this particular embodiment, the probes 34 or sensors 22 may be spaced apart or may be positioned proximate to each other to affect a continuous energy around a circumference of the cuff 20.

As illustrated in FIG. 6, one or more power supplies 40 may be positioned in the ring or cuff 20 to power the ultrasound generator 30*a* or electrical generator 30*b* and probes 34. The power supplies 40 and probes 34 may be operatively coupled by an elastic, flexible and/or stretchable conductive material that permits continuous operation of the device or system 10 during adjustment of the cuff 20. In this particular embodiment, the housing may be eliminated and the ultrasound generator 30*a* or electrical generator 30*b* incorporated into the cuff 20. The design of this embodiment provides a slimmer profile that may be advantageous for use during a sexual event or encounter. It should be understood that this design may be incorporated into any of the embodiments described herein.

Figure 7:
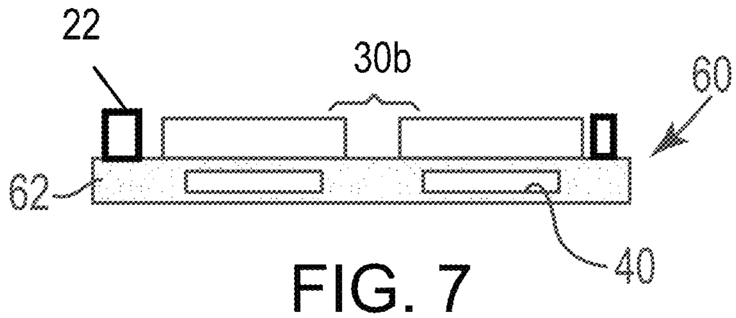
FIG. 7 is an end view of a disposable or reusable sexual dysfunction treatment patch with one or more power supplies and transducers, according to embodiments of the present invention.

As illustrated in FIG. 7, in an example embodiment of the invention, the device 10 may comprise a removable substrate or patch 60 that may be worn by a user to treat a sexual dysfunction, such as unintended sexual ejaculation, emissions, or a climax. The patch 60 comprises a base member 62 that can house or support one or more power supplies 40 and an ultrasound generator 30*a* or electrical generator 30*b*. The power supplies 40 are operatively coupled to one or more electrodes 30 that can be positioned and removably adhered against a user's tissue to deliver a nerve confusion therapy.

The patch 60, or any other device of the present invention, can include an actuating mechanism that uses the conductive nature of a user's skin to complete a circuit. For instance, once the device 10 is placed on the user the circuit is completed and the device 10 may be activated. When it is activated, the electrode 30 generate energy for the delivery of a therapy. Once the device 10 is removed, the circuit is broken and the electrodes 30 stop producing energy waves. Other actuating control mechanisms are also contemplated herein and may include an actuation switch that permits a user to turn the device on and off, or otherwise control output of the device as desired. The controller 50, described above, may also be used to control the patch 60.

As with other embodiments of the present invention, the patch 60 also includes one or more sensors 22 that are capable of detecting an approaching ejaculatory event and automatically applying the therapy. In an example embodiment of the invention, the sensors 22 are able to detect and correlate a physiological, chemical, or electrical phenomenon, or change in the penis or the perineum, to an approaching ejaculation. The controller 50 is then able to regulate the intensity and/or pattern of the energy being delivered to apply nerve confusion to the targeted nerve or nerves.

Figure 8:
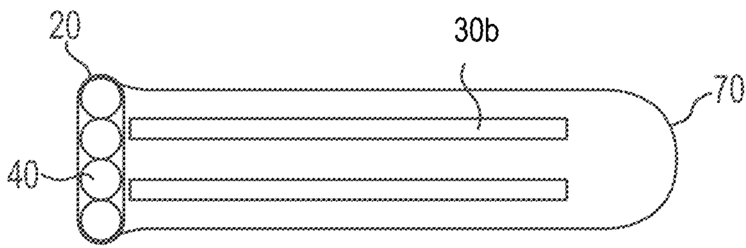
FIGS. 8-9 are side views of sexual dysfunction treatment systems having a sheath, according to embodiments of the present invention.
Figure 9:
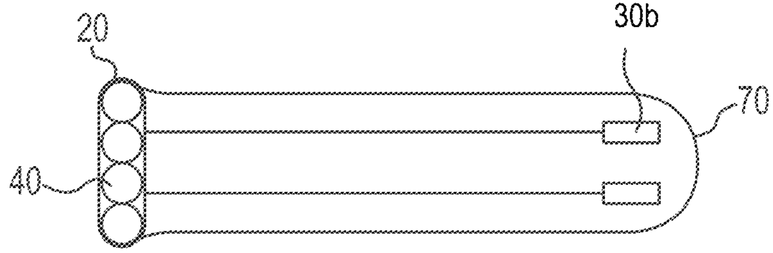

As illustrated in FIGS. 8-9, another embodiment of the present invention incorporates sexual dysfunction treatment with sexually transmitted disease ("STD") prevention. In these particular embodiments, the device or system 10 includes a sheath 70 incorporated with a ring or cuff 20. The sheath 70 includes one or more ultrasound generators 30*a* or electrical generators 30*b* that are located in a therapeutic location when worn by a user. The ultrasound generator 30*a* or electrical generator 30*b* may be located along a length or circumference of the sheath 70 (as illustrated in FIG. 8) or may be located in a particular location, such as the tip (as illustrated in FIG. 9) or base of the organ. The ultrasound generator 30*a* or electrical generator 30*b* may be operatively coupled to one or more power supplies 40 incorporated in the cuff 20. The embodiments of FIGS. 8 and 9 may be worn during a sexual event and then discarded. In another example embodiment, the sheath 70 may be cleaned and reused and the power supplies 40 may be recharged.

As discussed throughout, the cuff 20, patch 60, or sheath 70 may be worn during intercourse. It is also possible, however, that each may be worn during a non-sexual encounter treatment period. For instance, the cuff 20, patch 60, or sheath 70 may be worn under clothing, which permits a user to activate or switch the device 10 into a training mode, whereby a treatment session is activated and nerve confusion is applied to the targeted nerves for the purpose of training the nerves to delay an ejaculatory even. The training mode enables therapy to be applied at any time and at any location. One of the advantages of the present invention is that it is discrete and can be used to deliver therapy prior to a sexual encounter.

Figure 10:
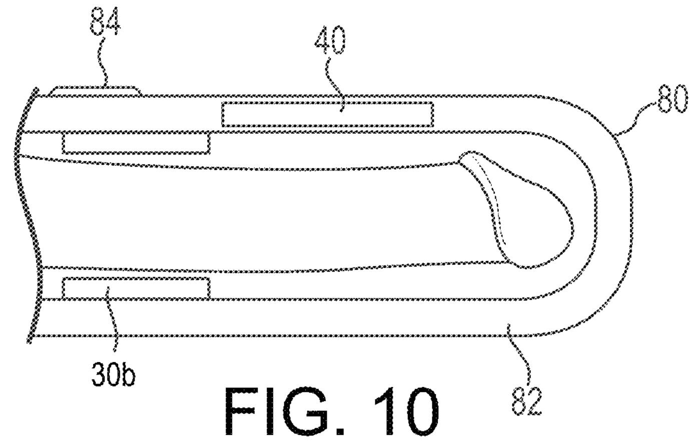
FIG. 10 is a side view of a sexual dysfunction treatment system having a sleeve, according to embodiments of the present invention.

As illustrated in FIG. 10, the device or system 10 of the present invention also includes a reusable therapy sleeve 80 that can be used to administer therapy. The sleeve 80 may be a generally rigid or flexible tube that has a closed end and an open end that is adapted to receive a penis of a user. The sleeve 80 includes side walls 82 that are able to support one or more ultrasound generators 30*a* or electrical generators 30*b* that are positioned to provide therapy to a user's penis. The ultrasound generator 30*a* or electrical generator 30*b* may be mounted to an inner surface of the sleeve 80, or may be embedded therein. The sleeve 80 may also include probes 34, so as to position the transducer(s) 30 a distance from the treatment location.

The side wall 82 of the sleeve 80 is also designed to support one or more power supplies 40 that are operatively coupled to the ultrasound generator 30*a* or electrical generator 30*b*. The power supplies 40 may be recharged wirelessly. The sleeve 80 may also include a power cord that allows a user to plug in the sleeve 80 to recharge the power supplies 40.

In one example embodiment of the invention, the sleeve 80 may include an actuator 84 to allow a user to control the power flowing to the ultrasound generator 30*a* or electrical generator 30*b*. The actuator 84 can comprise a switch mounted on the sleeve 80 or may comprise a wireless or wired controller 50 in operative communication. As discussed above, the controller 50 may comprise a mobile smart device such as a smartphone, watch, etc.

Figure 11:
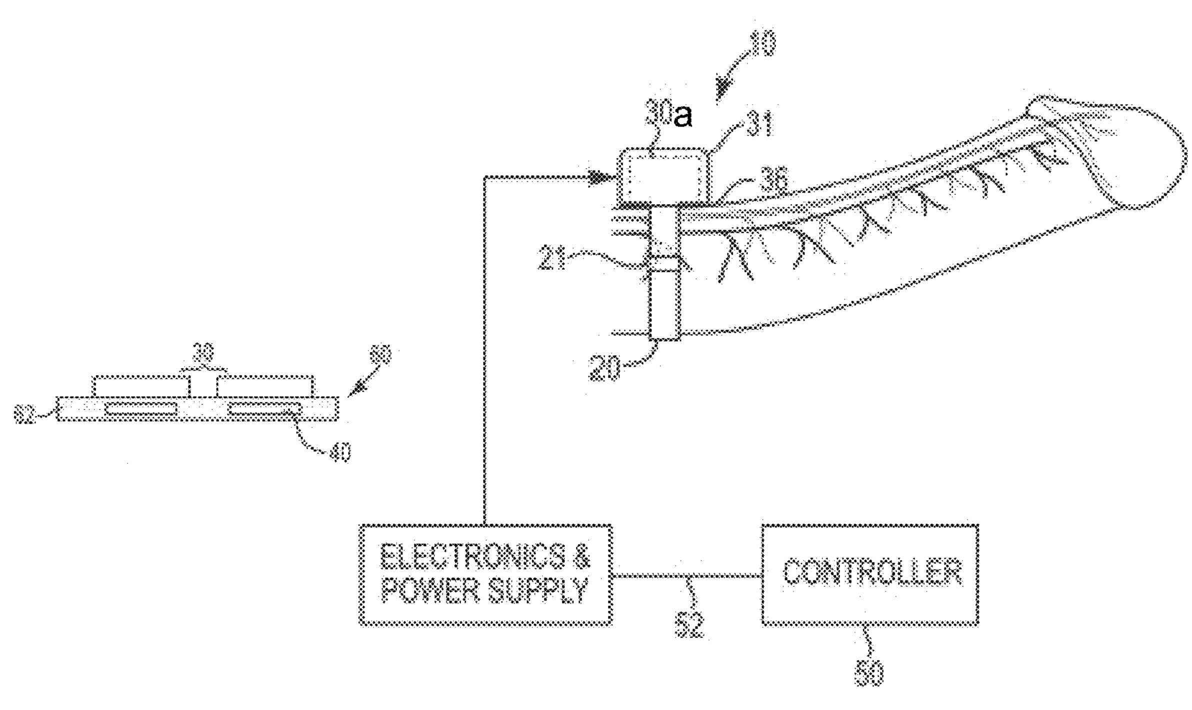
FIG. 11 is a side view of a multi-component sexual dysfunction treatment device, according to embodiments of the present invention.

In another example embodiment of the invention, as illustrated in FIG. 11, a multi-component device 10 is employed. In this embodiment, the patch 60 is placed on the perineum of the patient to deliver the therapy while the cuff 20 or other sensor 22 is placed in contact with or around the penis to sense the physiological changes in the penis. The cuff 20 or sensor 22 detects the physiological changes and sends the data to the controller 50, that then controls the patch 60 to deliver the therapy. The controller 50 is able to continuously monitor the cuff 20 or sensor 22 in order to regulate and control the therapy being delivered.

The controller 50 is used to control the intensity and/or pattern of energy being applied. The ability to continuously control the intensity and/or pattern of energy being applied enhances the nerve confusion to create an ultra-confusion of nerve stimulation. In a multi-component embodiment (e.g., electrodes on perineum and band around penis) the controller 50 is able to sense a change in the girth of the penis and the controller 50 can then can alter the electrical signals sent to the pudendal nerve by the electrodes. The opposite is also possible in an embodiment where the band also includes treatment components, such as electrodes or contacts.

Figure 12:
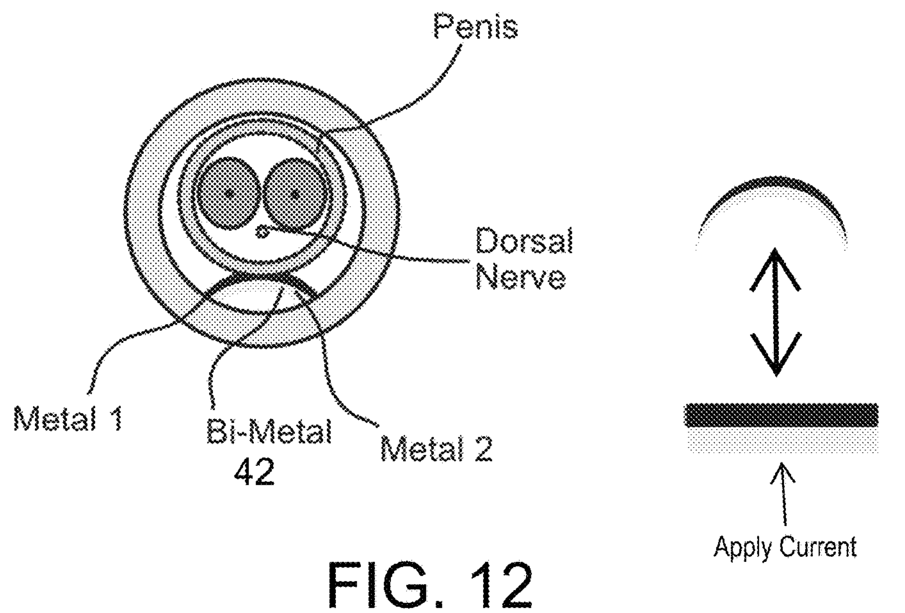
FIG. 12 is a cross-sectional view of a sexual dysfunction treatment system having compressible bimetal inner components in use, according to embodiments of the present invention.

As illustrated in FIG. 12, the cuff 20 may contain bimetal components or interiors 42, such that when a current is applied it is able to compress or contract, which in turn compresses or contracts the tissue of the penis. The contractions of the bimetal component or interior 42 is used to constrict or contract the muscle and/or nerves of the penis to cause nerve signal propagation. The controller 50 is able to continuously control and change the intensity, duration, and pattern of contractions on the penis. The variation in the contractions leads to ultra nerve confusion. The mechanical contraction can also be used in conjunction with the patch 60 that is placed on the perineum. The cuff 20 is able to deliver mechanical nerve confusion while the patch 60 provides electrical nerve confusion. The combination of therapies facilitates the delivery of ultra nerve confusion.

Figure 13:
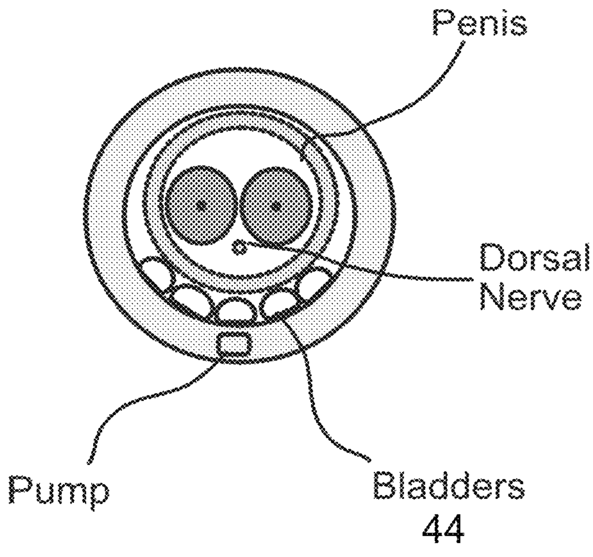
FIG. 13 is a cross-sectional view of a sexual dysfunction treatment system having inner bladders in use, according to embodiments of the present invention.

As illustrated in FIG. 13, other mechanical compressive device may also be used. For example, the cuff 20 may contain one or more inner bladders 44 that are inflatable and able to compress a portion of the penis to cause mechanical nerve confusion. The inflatable bladders 44 are in fluid communication with a pump that is controlled by the controller 50. The controller 50 is able to selectively inflate some or all of the inflatable bladders 44. The controller 50 is also able to control the inflation amount or intensity of the bladders 44. By controlling the intensity and the desired number and location of the bladders 44, the controller 50 is able to apply ultra nerve confusion to the targeted nerves. The cuff 20 with the inflatable bladders may also be used in conjunction with the patch 60.

Figure 14:
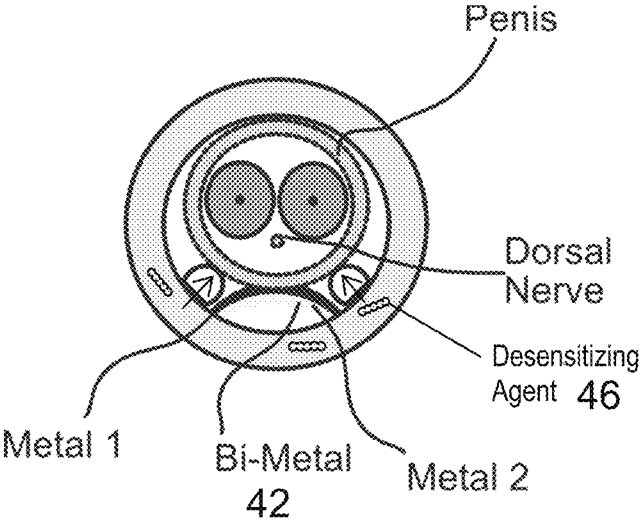
FIG. 14 is a cross-sectional view of a sexual dysfunction treatment system having a desensitizing agent/compound in an inner chamber in use, according to embodiments of the present invention.

As illustrated in FIG. 14, a desensitizing agent/compound 46 can be used in conjunction with the device 10 of the present invention to provided additional nerve blocking properties and further delay an ejaculatory event. The desensitizing agent/compound 46 can be applied to the dermis of the penis or perineum and then the device 10 can be activated to exert pressure or an electrical charge to the dermis to assist in penetration of the desensitizing agent/compound 46 into the penis. In another embodiment, the desensitizing agent/compound 46 can be stored in an interior of the cuff 20 and delivered through openings onto the skin or dermis of the penis being treated. Controller 50 is in operative communication with a pump or other like device that is used to deliver the desensitizing agent/compound. The desensitizing agent/compound 46 can also be used with the patch 60. Once a desensitizing agent/compound has been administered, the cuff 20 or patch 60 can be removed without concern for cross exposure to a partner.

In yet another embodiment of the present invention, controller 50 is able to control the delivery of a therapy based upon sensing a physiological state or action of a partner. For instance, if a partner increases the movement or intensity associated with intercourse, the controller 50 is able to control the cuff 20, patch 60, or a combination, to activate to delay an ejaculatory event.

Figure 15:
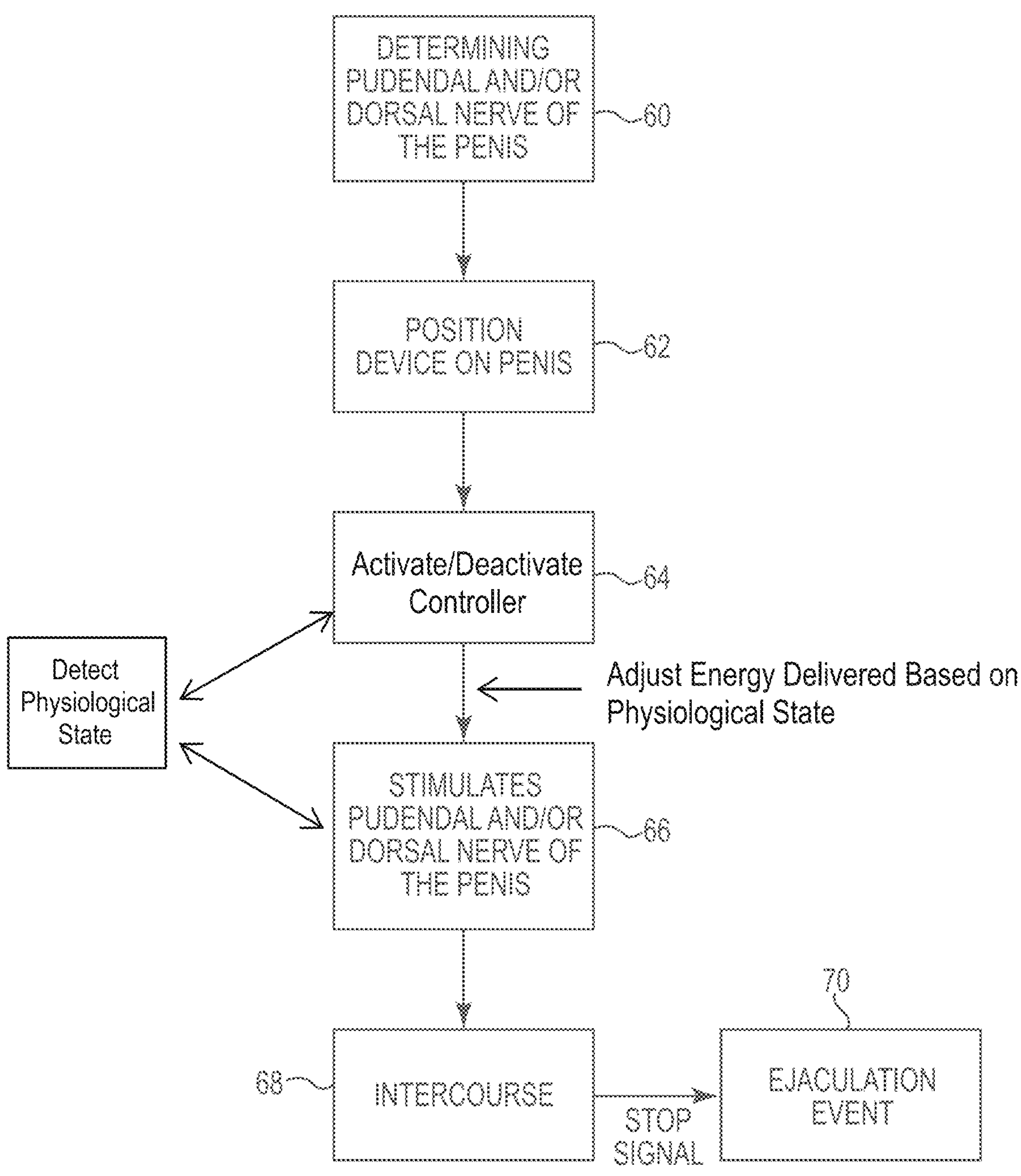
FIG. 15 is a diagram of an exemplary method of treating sexual dysfunction, such as premature ejaculation, according to embodiments of the present invention.
Figure 16:
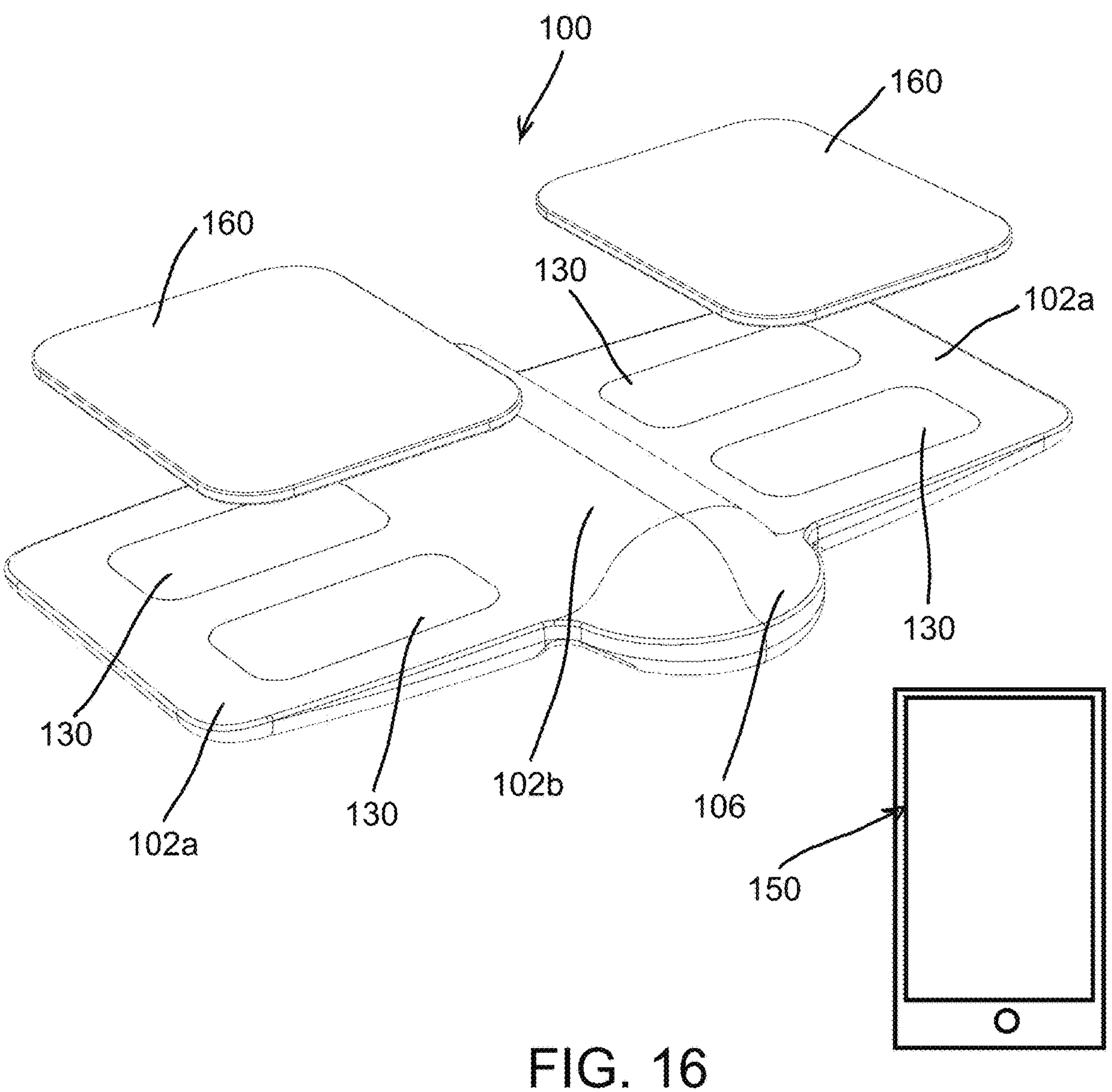
FIG. 16 is a perspective view of a hingeable sexual dysfunction treatment system, with a mobile device controller, according to embodiments of the present invention.
Figure 17:
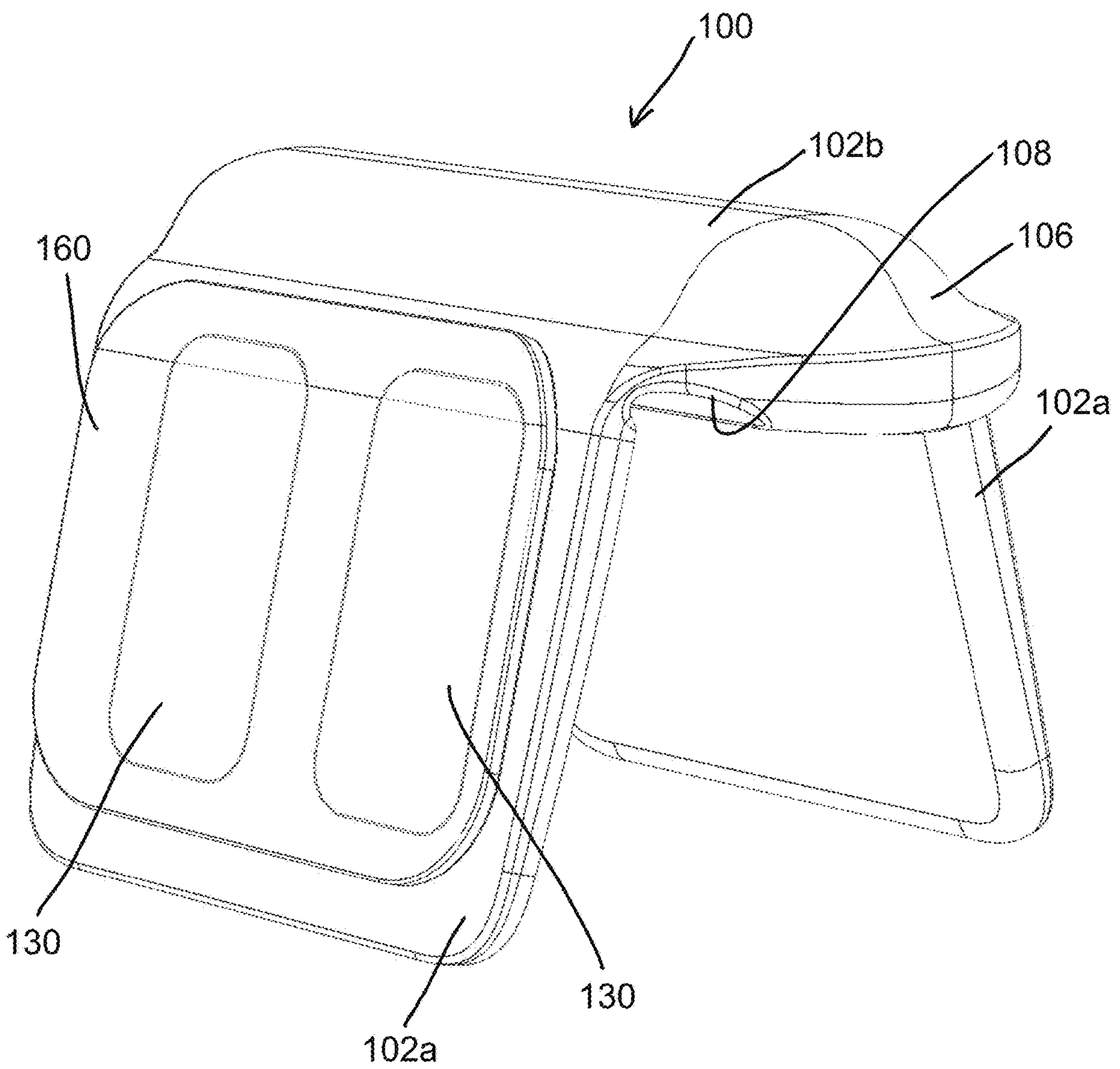
FIG. 17 is a perspective view of a hingeable sexual dysfunction treatment system, pivoted for use about living hinges, according to embodiments of the present invention.
Figure 18:
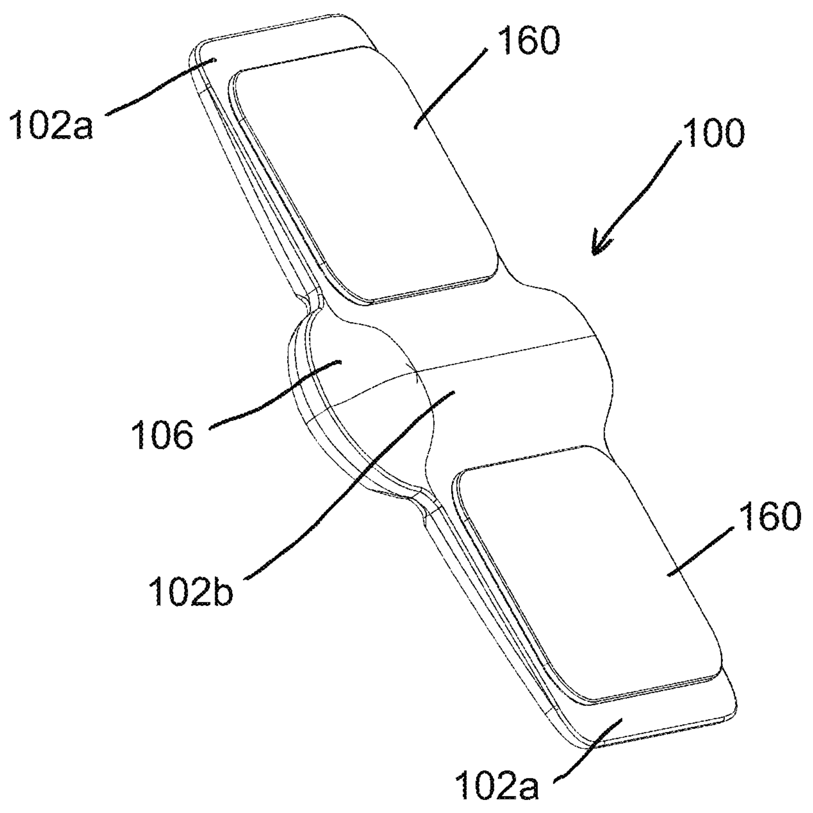
FIG. 18 is a top perspective view of a hingeable sexual dysfunction treatment system, according to embodiments of the present invention.
Figure 19:
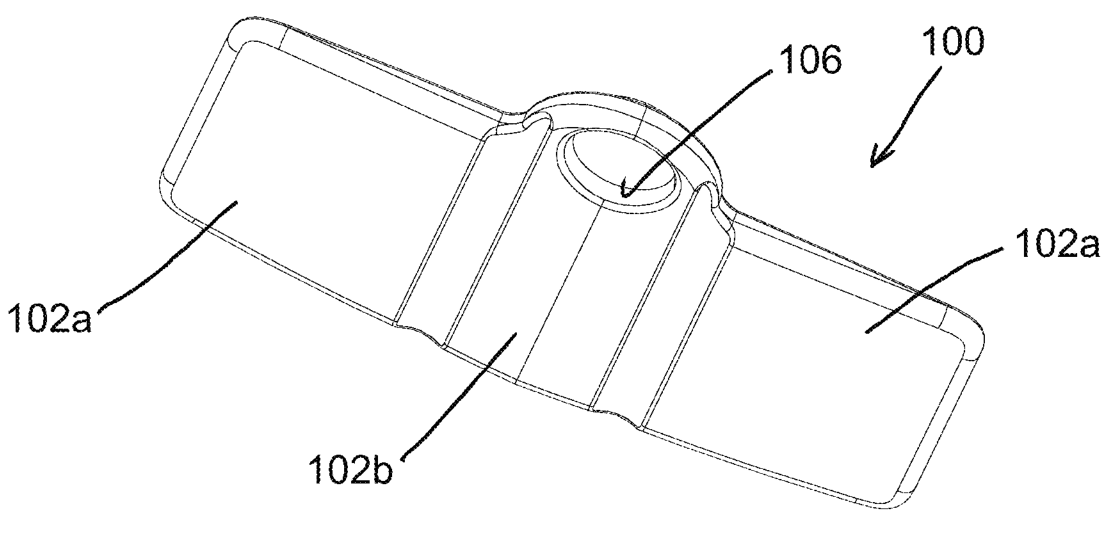
FIG. 19 is a bottom perspective view of a hingeable sexual dysfunction treatment system, according to embodiments of the present invention.
Figure 20:
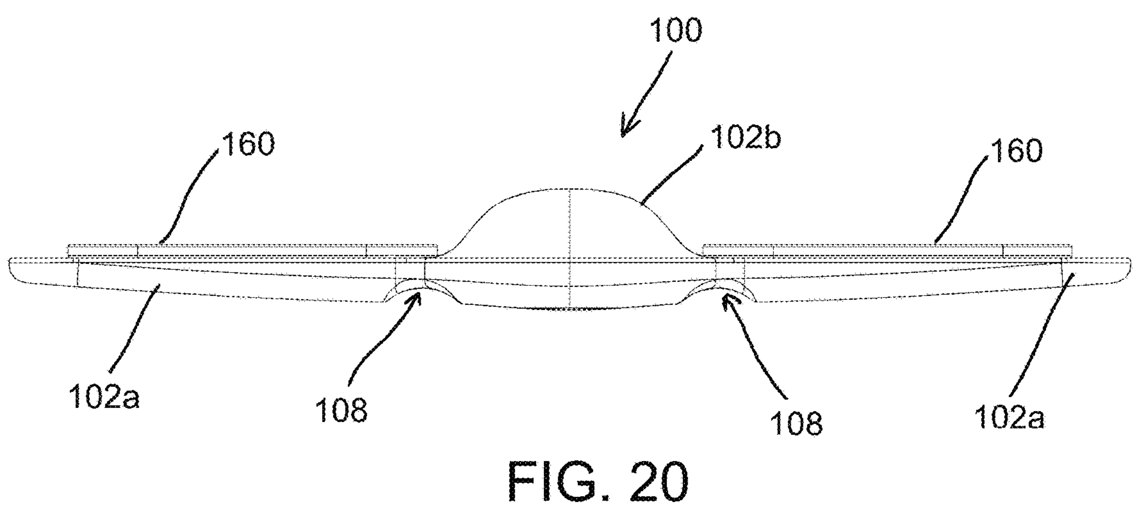
FIG. 20 is a front view of a hingeable sexual dysfunction treatment system, according to embodiments of the present invention.
Figure 21:
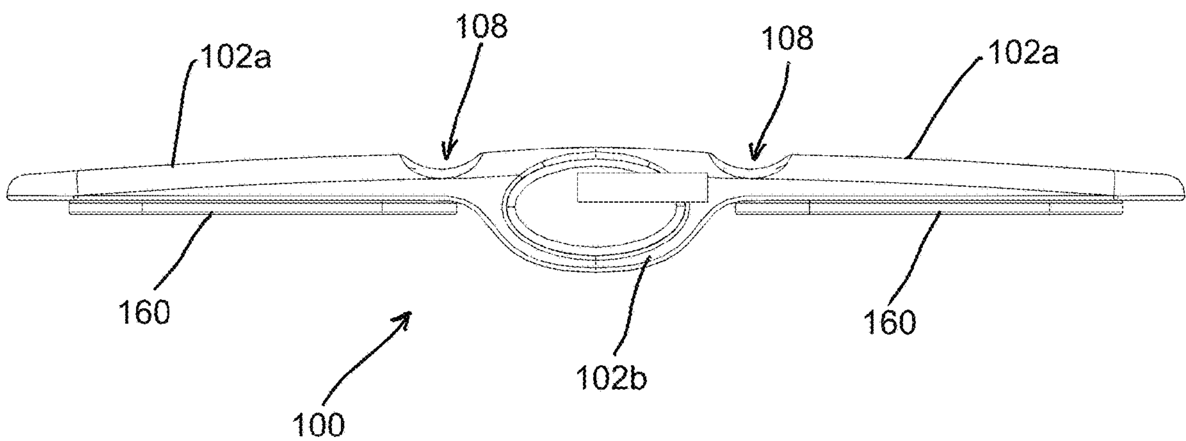
FIG. 21 is a back view of a hingeable sexual dysfunction treatment system, according to embodiments of the present invention.
Figure 22:
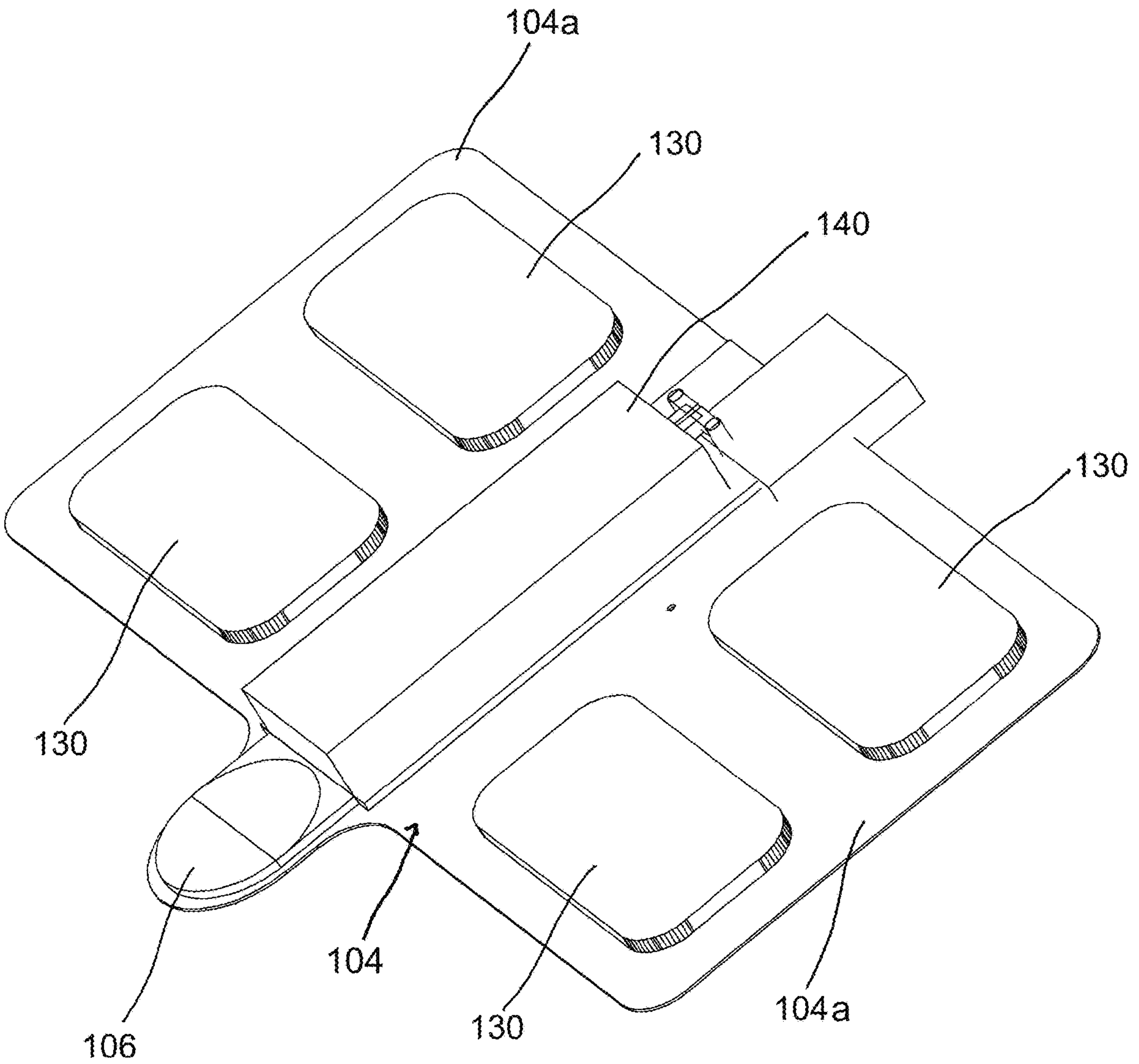
FIG. 22 is a top perspective view of a circuit board element for a hingeable sexual dysfunction treatment system, according to embodiments of the present invention.
Figure 23:
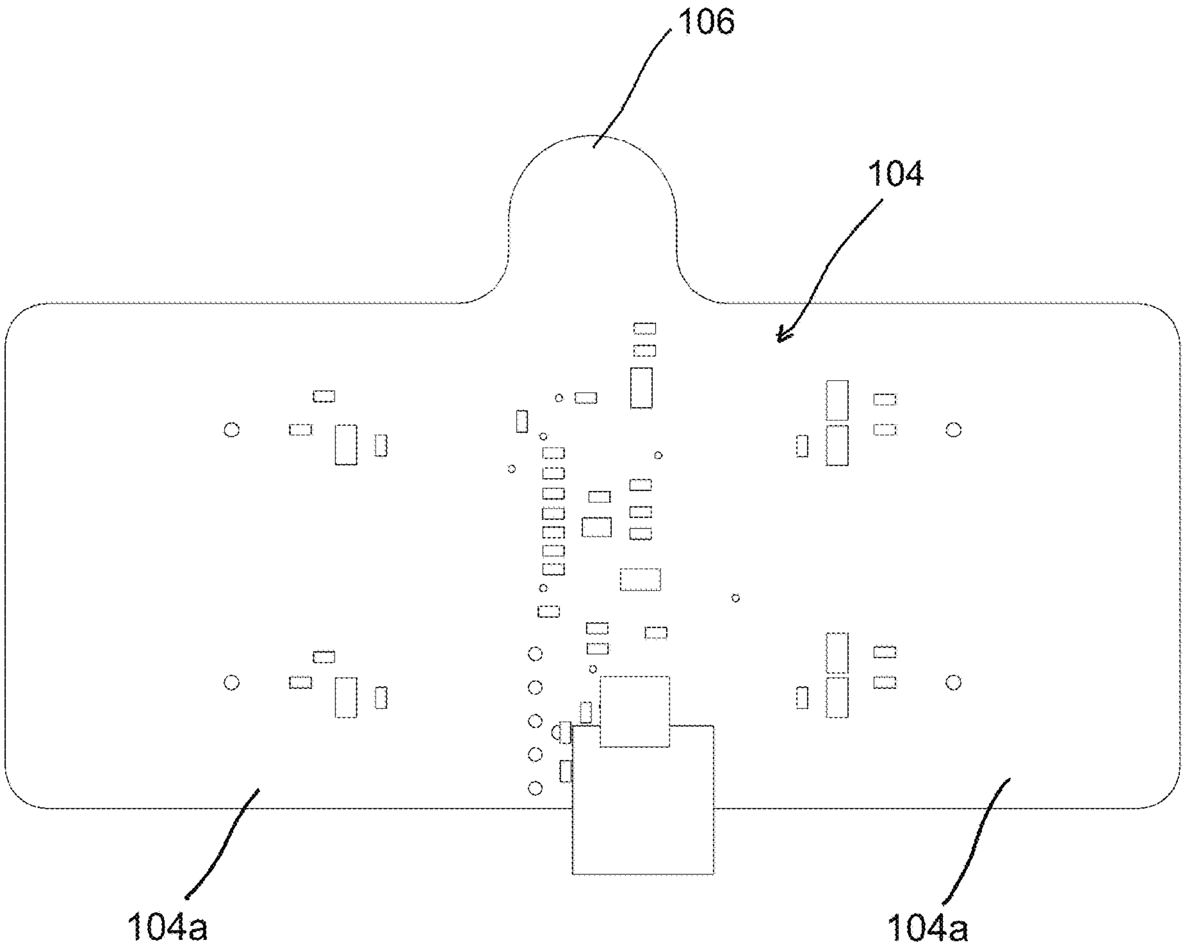
FIG. 23 is a bottom view of a circuit board element for a hingeable sexual dysfunction treatment system, according to embodiments of the present invention.

In use for various embodiments, as detailed in FIG. 15, a user or physician locates the dorsal or pudendal nerve of the penis or pudendal nerves of the penis at step 60. The user or their partner then positions the cuff 20, patch 60, sheath 70, or sleeve 80 on the penis at step 62 such that the one or more transducers 30 are placed proximate the nerve to be treated. In some embodiments, the user or their partner may then remove the film 38A, 38B from the coupling member 36 and position the coupling member 36 between the emitting surface 34 of the transducer 30 and the penis. In step 64, the user or their partner may then use the controller 50 or actuator 84 to activate the one or more transducers 30. The ultrasound generator 30*a* then emits sound waves 34, as shown in step 66. If the device 10 is being used during intercourse, the user and their partner can begin to have intercourse at step 68. Once either the user or partner wants to permit the treated user to ejaculate, the user or the partner may use the controller 50 to switch off the one or more transducers 30 (e.g., ultrasound generator 30*a*), thereby ceasing the sounds wave 34 and permitting the user to ejaculate at step 70.

In one embodiment of the invention, the device 10 is capable of increasing or decreasing the intensity of the therapy over a particular period of time. For instance, the device 10 is able to apply an amount of therapy, for example sound energy or electrical energy, which is not perceptible to a patient or user. The device 10 is then able to incrementally increase the intensity of the therapy to a pre-set level. After a certain period of time, the device 10 is able to incrementally decrease the intensity of the therapy. The therapy is capable of cycling the therapy levels for a period of time. In another example embodiment of the invention, a user or third party is able to manually adjust the intensity level and/or duration of the therapy session.

In still another embodiment of the invention, the device 10 may be implantable into a patient. The implantable device or system includes a biocompatible housing, internal therapy circuitry such as an ultrasound producing or electrical producing system. Leads may be implanted and disposed proximate a nerve, such as the dorsal nerve or pudendal nerve of the penis, that is capable of treating premature ejaculation.

The implantable system may be implanted in an office setting by using a delivery system that includes a delivery needle that may be inserted into the pubis region of a patient. In one example embodiment, the delivery needle may be inserted into a patient's uretha to deliver the system 10 into the patient's pubis. In yet another example embodiment, the delivery needle may be inserted transabdominally to deliver the system into the pubis region of the patient. The device 10 may be positioned in an anterior portion of the pubis or the base of the penis such that it is positioned proximate the dorsal nerve or pudendal nerve. Ideally, the device 10 is positioned proximate the dorsal nerve of the penis or pudendal nerve and may be activated transdermally by the controller 50. In the implantable embodiment, the ultrasound generator 30*a* or electrical generator 30*b* includes a rechargeable power supply that can be recharged transdermally (e.g., wirelessly). One of the advantages of the implantable embodiment is that a user's partner is unaware of the use of the system 10.

In another embodiment of the invention, as illustrated in FIGS. 16-27, a foldable, flexible, or hingeable device 100 can include a housing 102, a circuit board element 104, one or more electrodes or pairs of electrodes 130, and a power supply 140 (e.g., battery). The housing can include foldable wings or electrode containment portions 102 a and a central body portion 102 *b*. The device 100 is hingeable at living hinge portions 108 such that the device 100 can be selectively manipulated and placed with the electrodes 130 contacting tissue for stimulation. Further, an actuation mechanism 106 may be provided, which may comprise a button, touch sensor/interface, or other actuation mechanism. The actuation mechanism 106 can be pressed to turn the device 100 on and off, pressed or tapped to increase or vary stimulation, and the like. The power supply 140 and other component and circuitry can be housed within the central body portion 102 *b*.

The circuit board element 104 is contained within the housing 102, with foldable circuit portions 104*a* secured within the foldable wing portions 102*a* such that the electrodes 130 extend out from the wing portions 102*a* (e.g., via openings or apertures in the housing 102) for positioning and contact with patient tissue. The foldable portions 104*a* fold or pivot at circuit hinge portions 104*b* (e.g., FIG. 24).

The housing 102 can comprise of one or more layers of a flexible material such as a woven fabric, a plastic strip (such as PVC, polyethylene or polyurethane), or a latex strip. The internal components of the device 100 such as the circuit board element 104 and the electrodes 130 can be sandwiched between one or more layers. The housing 102 can comprise one or more openings proximate the electrodes 130 to allow or permit the electrodes to contact a user's skin. The housing 102 can also comprise conductive portions positioned over the electrodes 130 to allow for the electrodes to be protected but allow for the stimulation treatment to pass through the conductive material and onto the user's skin. The housing 102 can comprise any material that is disposable or can be cleaned or sterilized.

In another embodiment of the present invention, the housing 102 can comprise a molded flexible housing manufactured from a PVC, polyethylene or polyurethane material. The housing 102 has an interior configured to hold the circuit board element 104 and the electrodes 130. The molded housing 102 can also include openings or recesses for holding the electrodes 130, sensors, switches, and other features that are in operative communication with the device 100.

In one example embodiment of the present invention, the electrode containment portions 102*a* can have a thickness generally less than, greater than, or equal to a thickness of the central body portion 102*b*. The variation in the thickness of the electrode containment portions 102*a* can aid in enabling their flexing with respect to the central body portion 102*b*. The housing 102 can also comprise one or more web portions extending between and connecting the electrode containment portions 102*a* and the central body portion 102*b*. The web portion can have a thickness generally less than a thickness of the electrode containment portions 102*a* and the central body portion 102*b* to facilitate easier flexing of the electrode containment portions 102*a*.

In operation, the device 100 provides non-uniform and changing effective electrical stimulation timing of pulses with varying effective frequencies to "confuse" nerves and receptors involved in the ejaculatory process. The targeted neural network runs between the base of the penis and the spinal cord, within the region of the perineum. This is the anatomical area closest to those nerves and receptors involved in the ejaculatory process. There are other excitable tissues in the region that may receive electrical stimuli as well via the device 100. The device 100 is placed transperineally, with the electrodes 130 crossing the plane of nerves running parallel with the urethra.

The electrical stimulation of the device 100 is directed through the electrodes 130 using a non-uniform selection from one electrode to another. This stimulation pattern results in varying length pathways and a variance of time and physical distance for stimulations contacting those nerves and receptors. This results in an "ultra" neural stimulation at various times and directions within the ejaculatory neural network, thereby providing a varying of absolute and relative refractory time periods as well as their baseline resting membrane potential. Stimulations occur over varying parts of the refractory periods of the excitable cells in the perineal region, thereby resulting in neuromodulation of the ejaculatory process via neuro-confusion. This "ultra confusion" is imparted on the nerves and receptors, which promotes a modulation of nerve signal conduction, which results in time prolongation of ejaculation. Because the stimuli are constantly varying, there is a dramatic reduction or elimination of neurologic adaption to electrical signals, as well as a more effective neural modulation of the pathway.

The device 100 can be controlled and adjusted with a remote or mobile device 150, such as a smartphone and executed mobile app, in operative wireless communication with the circuit board element 104. The mobile app can receive feedback, monitor operation, log device and treatment information and data, analyze device and treatment information and data, and the like. The mobile device 150 can be used and operated by the patient, the patient's partner, and other authorized third parties.

Conductive electrode gel pads 160 are provided for placement and adherence over the one or more of the electrodes 130 during use. A single gel pad 160 can cover a single electrode 130, or two adjacent electrodes 130. The gel pads 160 can be replaced between uses of the device 100. The housing 102 of the device 100 can include a raised ridge portion that extends about the electrode containment portions 102*a* and 102*b*. The raised ridge portion aids a user in positioning the gel pads 160 over the electrodes 130.

While the device 100 of the invention is described as being reusable, it is also contemplated herein that the device 100 can be manufactured to be a single-use disposable item.

Figure 24:
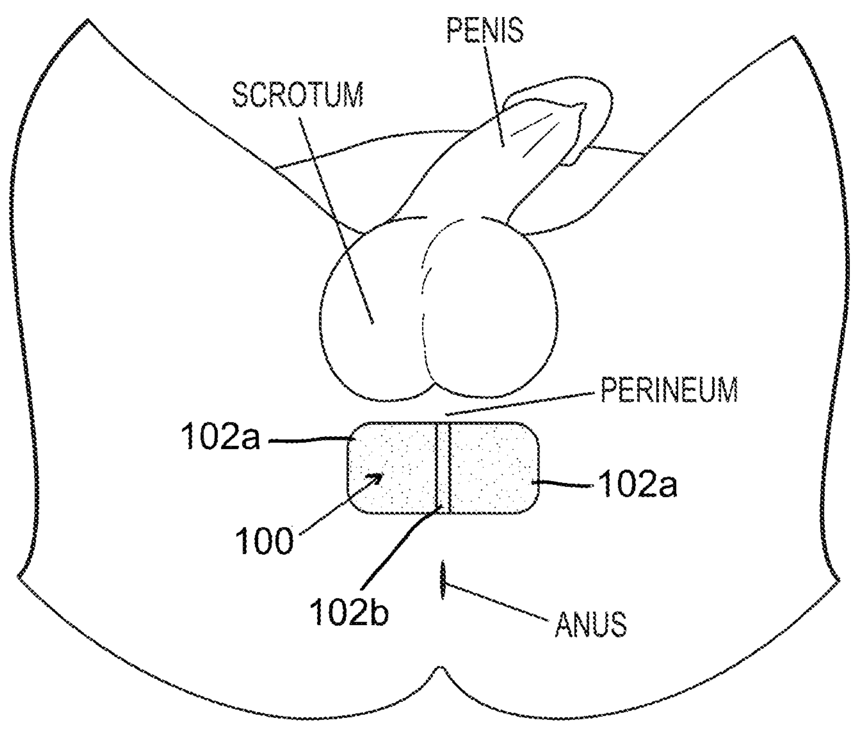
FIG. 24 is a view of the initial anatomical placement of a hingeable sexual dysfunction treatment system, according to embodiments of the present invention.
Figure 25:
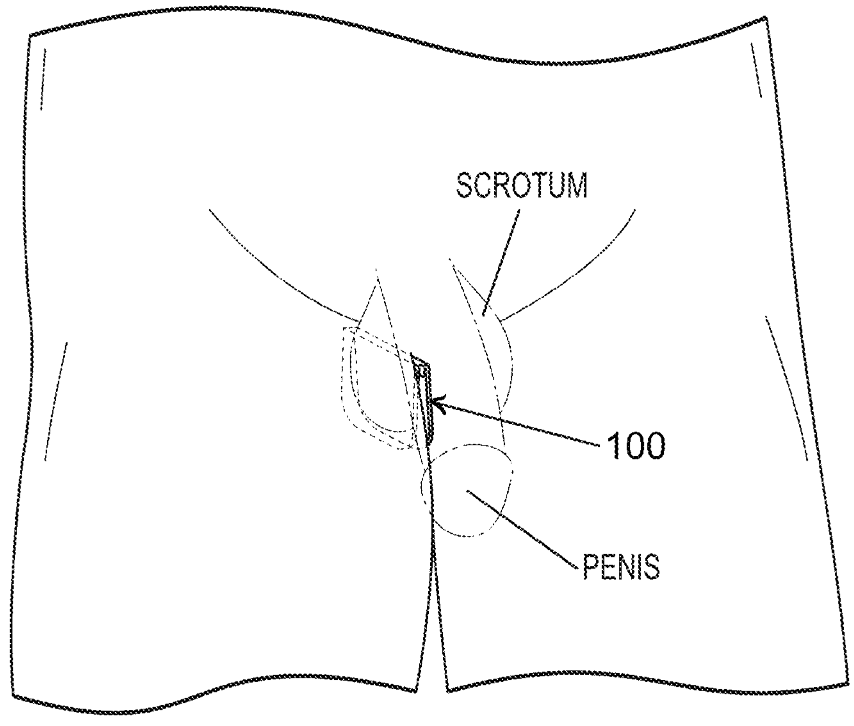
FIG. 25 is a view of hinged or pivotal therapeutic placement of a hingeable sexual dysfunction treatment system, according to embodiments of the present invention.

FIGS. 24-25 show the device 100 in use, placed on an exemplary male patient to facilitate effective treatment and therapy. FIG. 24 demonstrates the initial application of the device 100 in a generally non-hinged configuration at the perineum. FIG. 25 depicts the device 100 after hingeable placement at the perineum.

Figure 26:
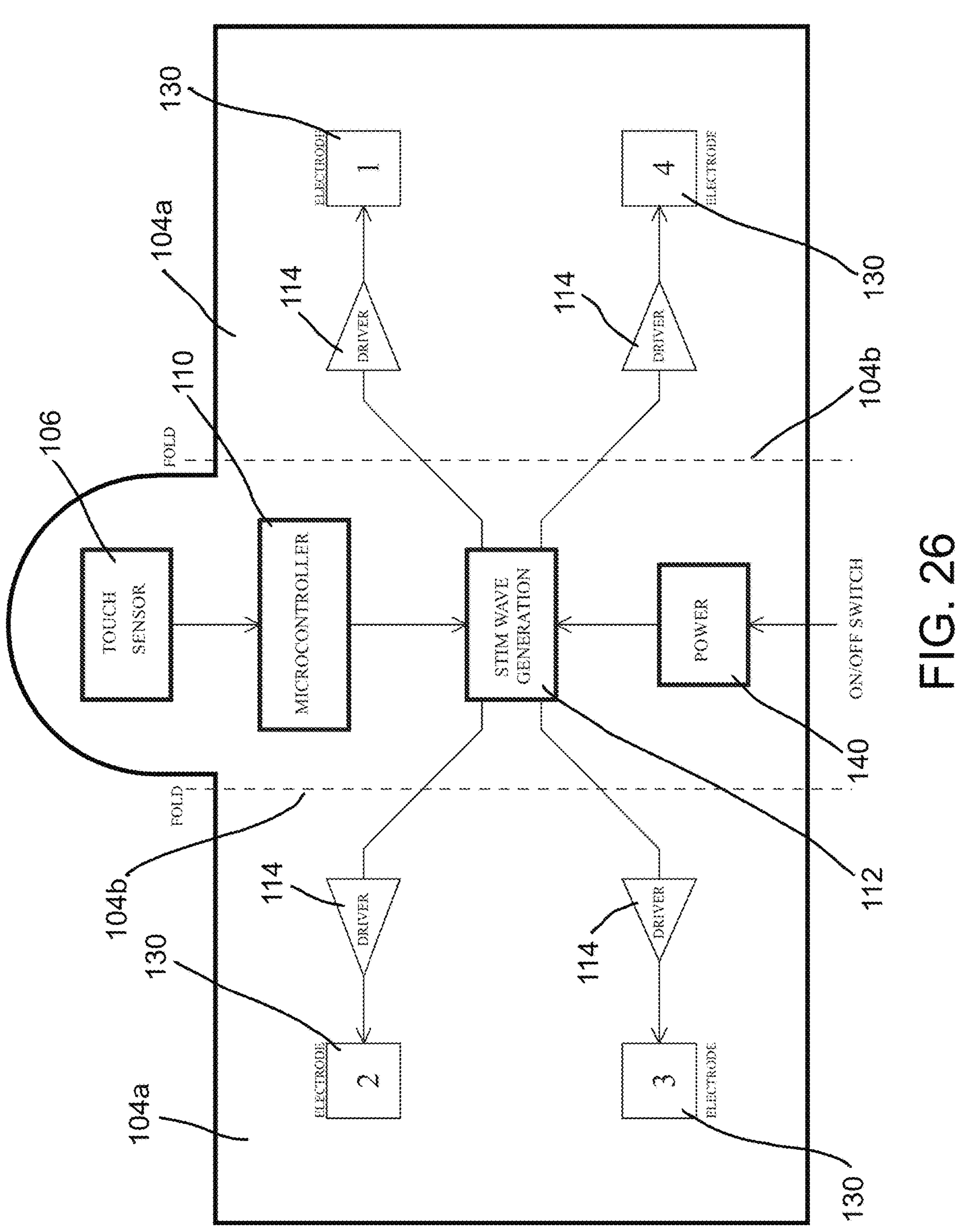
FIGS. 26-27 are schematic block diagrams of a circuit board elements and operative components and features for a hingeable sexual dysfunction treatment system, according to embodiments of the present invention.
Figure 27:
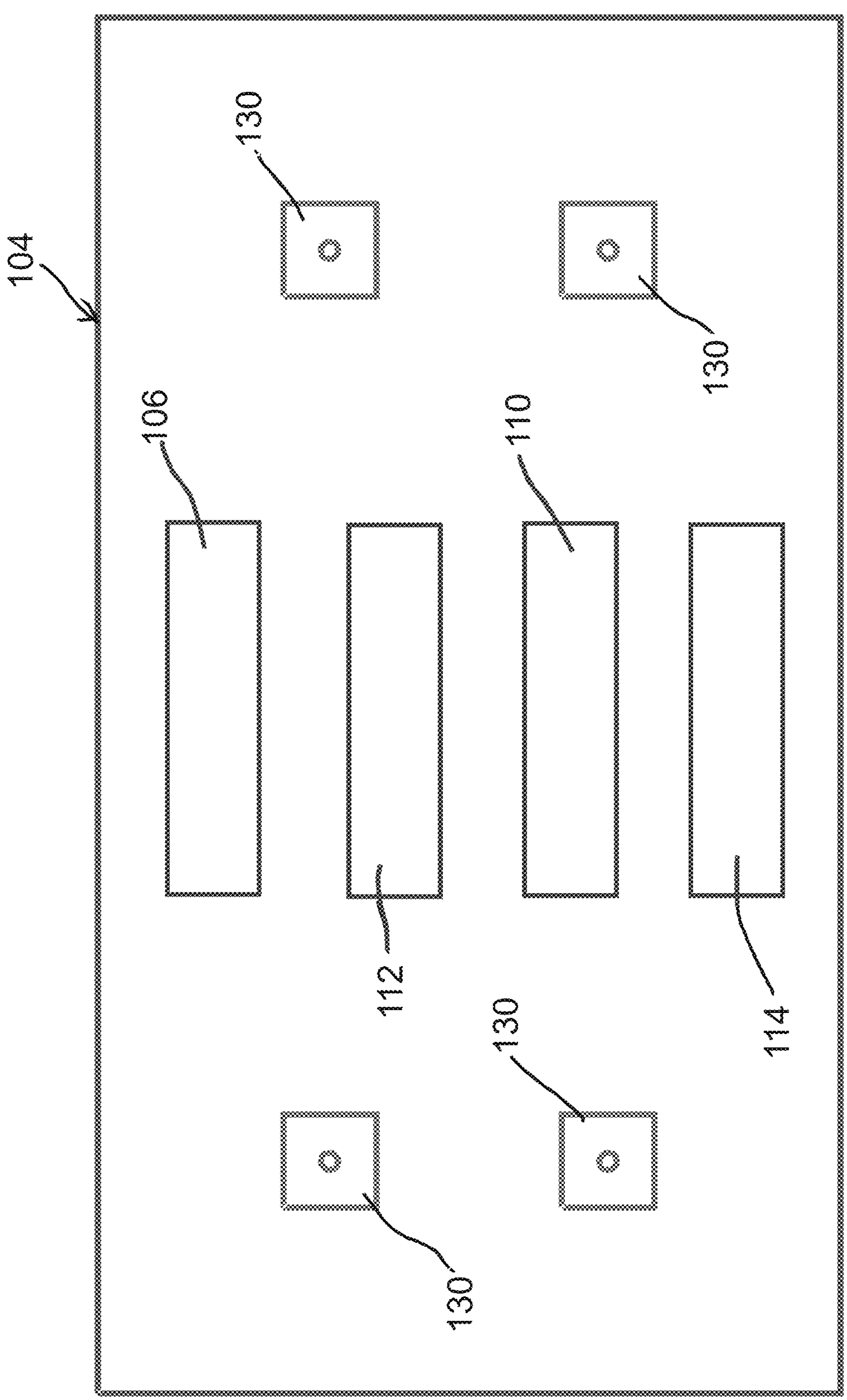

As shown in the schematic diagrams of FIGS. 26-27, embodiments of the device 100 include a an actuation mechanism 106, which may be a button, switch, or a touch sensor; a microcontroller 110, a stim wave generator 112, a power source 140, a plurality of stim drivers 114, and the plurality of electrodes 130. The power source 140 of the device 100 used to control the components of the device can be rechargeable. As such, the device 100 can include a charging port or wireless charging technology. In another example embodiment of the present invention, the power source 140 can be charged by wireless transmission through the one or more electrodes 130. In this way, the one or more electrodes 130 are able to provide a dual function of providing treatment and charging the power source 140. The device 100 can include a wireless charger that is able to interface with a portion of the device, or one or more of its electrodes 130 to charge the power source 140.

The onboard power source 140 allows the device 100 to generate four stim vectors through the electrodes 130 that vary in voltage and frequency. For example, the vector sequence can include the following pattern: electrode 1 to electrode 2; electrode 1 to electrode 3; electrode 4 to electrode 3, and electrode 4 to electrode 2. This pattern can be repeated or alternate between different patterns. A user selected voltage target changes the pulse frequency as well. Other effective therapeutic vector patterns and control adjustments can also be utilized without deviating from the spirit and scope of the present invention. For instance, the vector drives can be random or nearly random, the voltage, frequency and other vector patterns can be changed, a sequence or modulate voltage and/or frequency can be adjusted to obtain the highest level of neural confusion, voltage and frequency and applied modulations can be independently controlled, and stimulation and un-stimulation (or varied with a pattern) can occur that results in triggering the final ejaculation event via user control.

The device 100 is able to vary any of its parameters to aid in the "ultra confusion" of targeted nerves and pathways. The following are some examples of device parameters that can be varied:

Voltage and/or current levels
Voltage and/or current duration
Stim delivery frequency or period
Energy delivered
Impedance
Applied stim vector pattern and sequencing
Modulation of one or more of the above variables The present invention can also include one or more sensors that are able to sense an approaching ejaculatory event and then alter or modulate one of the above device parameters in order to provide effective stimulation therapy to delay the ejaculation. In one example embodiment, the electrodes 130 are also capable of acting as a sensor. In this embodiment, the electrodes 130 are able to sense a change in the skin potential that signals an approaching ejaculatory event. Other sensors may also be employed. For instance, stretch sensors can be used to detect the peristaltic waves or contractions of the penis. These contractions typically precede and coincide with an ejaculation. When a peristaltic contraction is detected the device 100 can modulate the therapy, thereby confusing the nerves until the peristaltic contractions stop. This process can be repeated until the user or their partner desires the ejaculatory event to occur, at which point they can turn off or reduce the therapy being delivered.

Sensors for detecting physiological and device parameters can include accelerometers, stretch sensors, impedance sensor—(may change nearing the event or in relation to other factors), temperature sensor, motion sensors (1,2 and 3D accelerometers for force, distance, rep rate, etc.), photosensors with or without LED light source (e.g., to sense heart rate, blood flow rate), and/or pressure sensors (e.g.,: measure blood pressure or changes in penis diameter). Other sensors and detection devices are also considered to be within the spirit and scope of the invention.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. A system for altering an approaching sexual event, comprising:
a housing comprising:
a central body portion;
first and second hinge portions being disposed on respective opposite sides of the central body portion;
first and second electrode containment portions disposed on respective opposite sides of the central body portion and attached to the respective first and second hinge portions;
wherein the first and second electrode containment portions are pivotally displaceable relative to the central body portion at the first and second hinge portions respectively extending between the central body portion and the first and second electrode containment portions respectively, and wherein the first and second hinge portions have a thickness less than a thickness of the central body portion and the first and second electrode containment portions;
circuitry disposed in the housing and configured to generate electrical stimulations;
a power supply disposed in the housing and in operative communication with the circuitry; and
at least first and second electrodes in operative communication with the circuitry to deliver the electrical stimulations, wherein the first electrode is disposed on the first electrode containment portion and wherein the second electrode is disposed on the second electrode containment portion, with the at least first and second electrodes pivotally displaceable for transperineal tissue contact.

2. The system of claim 1, wherein the at least first and second electrodes further include third and fourth electrodes.

3. The system of claim 2, wherein the first and third electrodes provide a first electrode pairing and the second and fourth electrodes provide a second electrode pairing.

4. The system of claim 3, wherein the first electrode pairing is provided with the first electrode containment portion and the second electrode pairing is provided with the second electrode containment portion.

5. The system of claim 1, further including a controller comprising a button that is configured to communicate with the circuitry to control a pattern of the generated electrical stimulations, wherein the controller is disposed on the housing.

6. The system of claim 5, further including a wireless smartphone including an executable mobile application, wherein the executable mobile application is in operative communication with the controller.

7. The system of claim 1, further including an actuator comprising a switch coupled to the housing and operatively coupled to the circuitry, wherein the switch is configured to receive manual manipulation to control power to the circuitry.

8. The system of claim 7, wherein the actuator is configured to adjust stimulation intensity to at least the first and second electrodes.

9. The system of claim 1, wherein the first and second hinge portions comprise living hinges disposed on respective opposite sides of the central body and extending parallel to and along first and second sides of the central body portion.

10. A reusable system for altering an approaching ejaculation event, comprising:

a housing comprising:

an elongate central body portion, first and second electrode containment portions disposed on respective opposite sides of the central body portion;

first and second hinge portions disposed on respective opposite sides of the central body portion and extending along a length of and parallel to the central body portion;

wherein the first electrode containment portion is configured to be pivotally displaceable relative to an axis of the central body portion at the first hinge portion, and the second electrode containment portion is configured to be pivotally displaceable relative to an axis of the central body portion at the second hinge portion, wherein the central body portion has a thickness greater than a thickness of the first and second electrode containment portions;

therapy circuitry configured to deliver electrical stimulation, wherein the therapy circuitry is disposed within the housing;

a power supply disposed within the housing and in operative communication with the therapy circuitry;

a button disposed in the housing and configured to communicate with the therapy circuitry to control and alter a stimulation pattern of the electrical stimulation; and one or more electrode pairs disposed on the housing, each of the one or more electrode pairs being in operative communication with the therapy circuitry and the button, wherein the one or more electrode pairs are configured to transmit the electrical stimulation to deliver neuromodulation therapy in a perineal region.

11. The system of claim 10, wherein the button comprises a touch sensor configured to communicate with the therapy circuitry.

12. The system of claim 11, further comprising a remote mobile device including an executable mobile application, wherein the executable mobile application is in operative communication with the therapy circuitry.

13. The system of claim 10, further including at least one replaceable conductive pad positionable upon the one or more electrode pairs.

14. The system of claim 10, further including an actuator, comprising a switch, wherein the switch is disposed on the housing and in operative communication with the therapy circuitry, and wherein the switch of the actuator is capable of manual manipulation.

15. The system of claim 14, wherein the switch is configured to receive manual input for controlling the power to the therapy circuitry.

16. The system of claim 10, wherein the first and second hinge portions comprise living hinges disposed on respective opposite sides of the central body and extending longitudinally along first and second sides of the central body portion.

17. The system of claim 10, further comprising one or more sensors in operative communication with the therapy circuitry to detect the approaching ejaculation event.

18. The system of claim 12, further comprising the mobile application on the mobile device in operative communication with the therapy circuit, the mobile device being configured to execute software for controlling stimulation output to the one or more electrode pairs.

19. The system of claim 18, wherein the software is configured to receive feedback from the therapy circuitry.

20. The system of claim 18, wherein the software is configured to monitor and control stimulation output via the therapy circuitry.

* * * * *